US005254381A

United States Patent [19]

Hoffmann et al.

[11] Patent Number: 5,254,381

[45] Date of Patent: Oct. 19, 1993

[54] LABEL-EQUIPPED SHEET

[75] Inventors: Donald J. Hoffmann, Elmhurst; Joseph J. Juszak, Crystal Lake, both of Ill.

[73] Assignee: Wallace Computer Services, Inc., Hillside, Ill.

[21] Appl. No.: 886,739

[22] Filed: May 21, 1992

Related U.S. Application Data

[63] Continuation-in-part of Ser. No. 705,313, May 24, 1991, abandoned, and a continuation-in-part of Ser. No. 705,325, May 24, 1991, abandoned.

[51] Int. Cl.[5] .......................... A61F 13/02; G09F 3/10

[52] U.S. Cl. .......................... 428/40; 428/41; 428/42; 428/43; 428/138; 283/81; 283/101; 40/299; 40/630

[58] Field of Search .......................... 428/40, 41, 42, 43, 428/138; 283/81, 101; 156/247, 257, 248, 268; 40/249, 630

[56] References Cited

U.S. PATENT DOCUMENTS 3,421,239 1/1969 Smith .................. 428/40
3,914,483 10/1975 Stipek, Jr. .................. 428/42
3,926,113 12/1975 Steidinger .................. 156/542
4,246,058 1/1981 Reed .................. 156/183
4,379,573 4/1983 Lomeli et al. .................. 428/42
4,479,838 10/1984 Dunsirn .................. 156/247
4,526,405 7/1985 Hattemer .................. 283/81
4,627,994 12/1986 Welsch .................. 428/41
4,664,416 5/1987 Steidinger .................. 283/81
4,749,432 6/1988 Ando .................. 156/257
4,833,122 5/1989 Doll .................. 428/40
4,865,669 9/1989 Schmidt .................. 428/41
5,006,191 4/1991 Schmidt .................. 156/268
5,074,595 12/1991 Hill .................. 283/81

FOREIGN PATENT DOCUMENTS 1-21896 12/1990 Japan .

*Primary Examiner*—Ellis P. Robinson
*Assistant Examiner*—Nasser Ahmad
*Attorney, Agent, or Firm*—Tilton, Fallon, Lungmus & Chestnut

[57] ABSTRACT

A method of making a label-equipped sheet and product in which an elongated release liner has one face thereof equipped with pressure sensitive adhesive and adhered to one surface of a base stock web, the base stock web being diecut in a closed perimeter within the confines of the release liner, the diecutting including a generally linear segment which is adjacent an area of the release liner free of release material to provide a longitudinally-extending liner band adhesively secured to the web.

5 Claims, 1 Drawing Sheet

Fig. 1
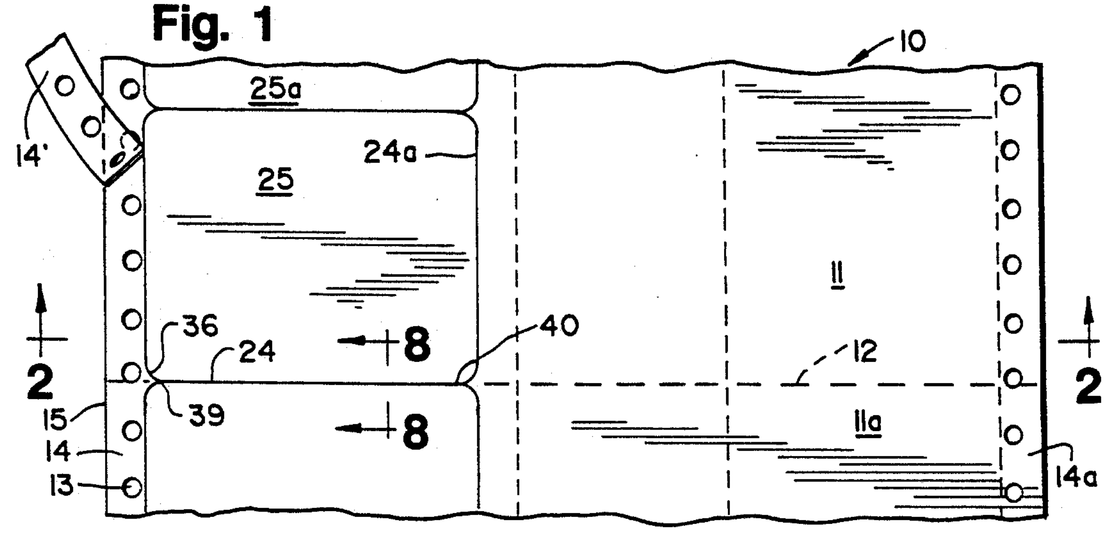
Fig. 2
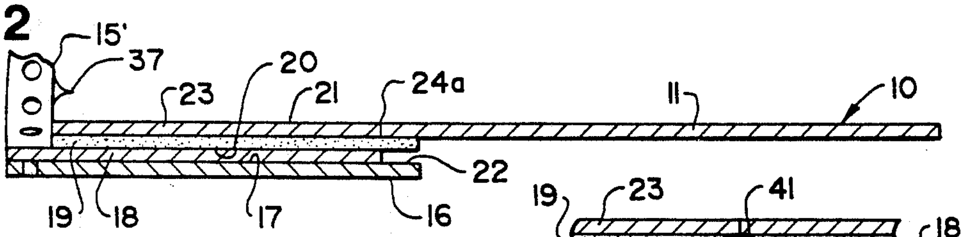
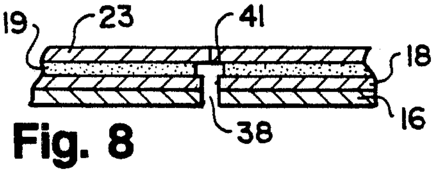
Fig. 8
Fig. 3
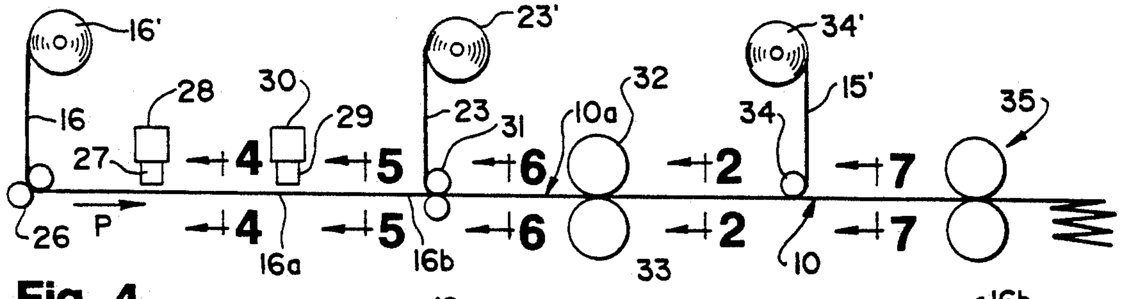
Fig. 4
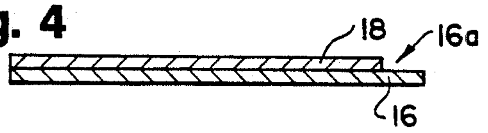
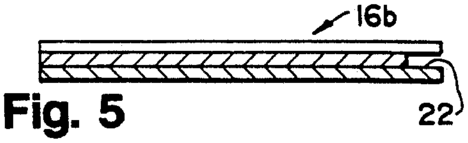
Fig. 5
Fig. 6
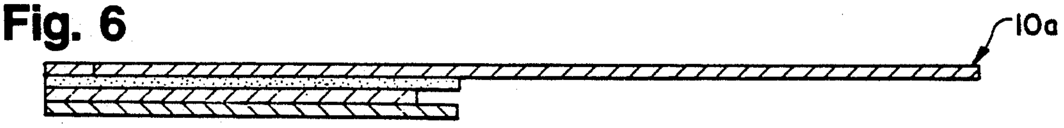
Fig. 7
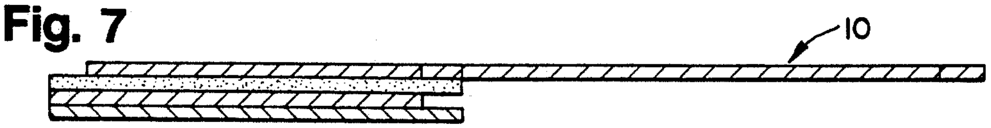

LABEL-EQUIPPED SHEET

This application is a continuation-in-part of co-pending applications Ser. Nos. 705,313 and 705,325 both filed May 24, 1991, now abandoned.

BACKGROUND AND SUMMARY OF INVENTION

This invention relates to a method of making a label-equipped sheet and product and, more particularly, to a sheet or form wherein the label is diecut from base stock constituting the sheet and held in place by a pressure sensitive adhesive-equipped release liner until needed for use.

It has become increasingly desirable to provide sheets generally and business forms particularly of minimal thickness for ease in processing through computer printers, especially table top personal computers with associated printers. One approach to achieve this has been to diecut the form itself to provide a removable label. This art is well known for diecut labels generally in U.S. Pat. Nos. 3,914,483 and 4,246,058 and for business forms in U.S. Pat. No. 4,379,573.

However, with the processing of sheets such as business forms through printers and the subsequent converting of the connected forms into a roll or a zig-zag pack, there arises the possibility of the release liner becoming detached. This exposes the pressure sensitive adhesive on the sheet with many undesirable consequences. The current trend of omitting adhesive along the edge of an attached member increases the possibility of undesirable detachment. Illustrative of this trend in the art is exemplified by U.S. Pat. Nos. 3,926,113; 4,526,405, 4,664,416 and 5,011,559. The drawbacks of the prior art are avoided by the invention.

According to the invention, the release liner is strongly adhered to the rear face of the wider label stock web along one longitudinal edge of the release liner. This is accomplished by providing the above-mentioned longitudinal edge free of release material——which is normally a silicone. This provides a band on the release liner where the adhesive between the liner and web can integrate the liner and web substantially permanently. When the web over the liner is perimetrically diecut to provide a label spaced slightly from the band, the label can be removed while the web and liner remain together. Thus, there is no exposed adhesive on the rear face to cause the label stock to undesirably adhere to some other surface or sheet.

It is known to provide a wider label stock web and diecutting it over a narrower release liner——as set forth as prior art in U.S. Pat. No. 4,627,994. However, the release liner did not have a longitudinally-extending edge band lacking the release coating——so it could not achieve the strong bond to the label stock web. From there, the art workers went away from the idea of a silicone free band. Instead, they went to separately attached webs as in the invention of the '994 patent and subsequent U.S. Pat. No. 4,696,843 and co-owned Pat. Nos. 4,865,669 and 5,006,191.

The invention also affords other advantages. For example, the invention makes easier the removal of the label from the label stock web. This is achieved by removing a longitudinally extending strip of liner which advantageously can be located adjacent the other longitudinal edge of the liner from edge that is equipped with the aforementioned band.

The details of the inventive method and construction can be seen in the ensuing specification.

BRIEF DESCRIPTION OF DRAWING

The invention is described in conjunction with the accompanying drawing, in which——

FIG. 1 is a fragmentary top plan view, partially in perspective of a portion of a continuous web such as business form string featuring one version of the invention;

FIG. 2 is an enlarged sectional view such as would be seen along the sight line 2—2 applied to FIG. 1;

FIG. 3 is a side elevational view (essentially schematic) of apparatus employed in the practice of the inventive method;

FIGS. 4–7 are transverse sectional views of the web/-webs advancing from left to right in FIG. 3 as would be seen along the various sight lines 4—4, 5—5, etc.; and FIG. 8 is a longitudinal sectional view taken along the sight line 8—8 of FIG. 1.

DETAILED DESCRIPTION

Referring to FIG. 1, the numeral 10 designates generally a string of interconnected business form lengths of the general type seen in co-owned U.S. Pat. No. 4,664,416. One fragmentary form length is designated 11 with the adjacent following length being designated 11*a*. It will be understood that the form lengths are produced continuously and conveniently converted to rolls or zig-zag folded packs for shipment. Lines of transverse perforation as at 12 define the ends of each form length.

The entire string is equipped with line holes 13 and a control punch margin 14 at least along one longitudinally extending side 15. As shown, line holes and therefore control punch margins, are normally provided along both longitudinal sides for better control of the web during both manufacture and subsequent processing through the computer printer——as seen in the '416 patent. However, in some instances the other control punch margin 14*a* can be omitted. When the base stock web is just a sheet, both margins are usually omitted, as would be the case with snap-out forms.

The form length 11 is equipped with a release liner 16 (usually a silicone coated ply) which can be appreciated from a consideration of FIG. 2. There, the release liner ply 16 has one face 17 equipped with a silicone coating 18 and over that a pressure sensitive adhesive 19. In this way the liner 16 is adhered to one surface 20 of the generally rectangular form length 11. This is the surface opposite to the surface 21 which is arranged uppermost normally——as for printing.

It will be noted that the silicone coating 18 does not extend to the inboard side of the liner 16——leaving an uncoated, longitudinally-extending band 22. This is of significant advantage in the use of the invention because it affords the adhesive 19 the opportunity to lock or freeze the release liner 16 to the label stock web 23 which makes up the form lengths 11, 11*a*, etc. In similar fashion, the release liner 16 is continuous——running from one form length to the next, but narrower. In other words, the liner 16 has a predetermined width and the web 23 has a width greater than that predetermined width.

A perimetric diecut is provided at 24 to define a generally rectangular label 25. A longitudinally extending portion 24*a* of the perimetric diecut 24 is spaced slightly inwardly of the band 22 (see FIG. 2). Thus, a slight error in adhesive application or web alignment will not interfere with ready removal of the label 25 inasmuch as it would be completely confined within the extent of the liner 16.

It is believed that the invention can be further appreciated from a consideration of the method of making the label-equipped sheet product.

INVENTIVE METHOD

Referring now to FIG. 3, a parent roll of liner material 16' is adapted to be unwound to provide the liner 16 which then proceeds along a horizontally extending path designated by the arrow marked P. The path normally is provided by side frames (not shown) which carry the various processing rolls. Thus, provided adjacent the path P is the roll 16' of the release liner web material such as a siliconed ply. The liner ply 16 is unwound from the roll 16' by means of an infeed 26 consisting of draw rolls and thereafter the ply 16 proceeds past a nozzle 27 for applying the silicone coating 18 to the face 17 (see FIG. 2) of the liner 16. The nozzle 27 is equipped with a solenoid operated control valve 28 which can be used to pulse the application of release material to the web 16. Thus, just downstream of the nozzle 27, the cross sectional condition of the ply **16*a* can be seen in FIG. 4**.

The web **16*a* now passes under another nozzle 29 with its associated control valve 30 by which adhesive is applied resulting in a web cross-sectional configuration designated 16*b* and which is depicted in FIG. 5. There it will be noted that the band 22** free of silicone coating is provided.

Still proceeding to the right in FIG. 3, the ply **16*b* is equipped with the web 23 which is provided by a parent roll 23' along with a suitable draw roll means 31. The condition of the composite web 10*a* downstream of the draw roll means 31 is seen in FIG. 6 and is very much the same as that seen in FIG. 2 except that the diecuts 24** have not yet been applied.

The diecuts are applied by a knife roll 32 (referring to the central portion of FIG. 3) operating against an anvil roll 33. At this juncture, the composite web is essentially similar to that depicted in FIG. 2.

In FIG. 2 as well as FIG. 1, there is a control punch margin 15' made up of the web 23 and associated adhesive seen in the process of being stripped away. This strip passes around an idler roll 34 and into a disposable roll 34' (see FIG. 3). At this juncture the composite web has the configuration seen in FIG. 7 and is designated generally by the numeral 10 reflecting the condition of the product as it is seen also in FIG. 1.

After the control punch margin 14' of the web 16 has been removed, the composite web product is passed into finishing means generally designated 35 which may either be folding rolls to impart a zig-zag configuration to the web or rewinding rolls to develop a convolutely wound roll product.

In summary, the inventive method for producing a label-providing business form includes the steps of providing a elongated liner 16 having one face 17 coated with release material 18 except for a band 22 free of the material along one liner longitudinal edge. The method further includes the provision of a label stock form 23 having a width greater than the width of the liner 16 and bringing the web and liner together with pressure sensitive adhesive 19 therebetween so as to strongly adhere the liner band 22 to the web 23 and with the web 23 extending laterally beyond the band 22. Thereafter, the web is perimetrically diecut as at 24 to provide a label 25 over the liner 16 and with the diecut longitudinal portion **24*a* spaced slightly away from the band 22**.

The composite label product is made advantageously in a continuous fashion as illustrated in FIG. 3 and usually makes use of control punch margins such as are seen along the longitudinal edges of the form 10 in FIG. 1. Also, the composite product is divided up into form lengths as at 11, **11*a*, etc. with transversely extending lines of perforation 12 between each form length. Depending upon the ultimate application, each form length may have a single label or a plurality of labels related longitudinally to each other. This latter is the situation in the illustration given in FIG. 1 where the fragment of the form length 11 is seen to include both a label 25 and a longitudinally related label 25*a*——see the upper left hand portion of FIG. 1**.

It is also advantageous to provide both the liner 16 and the web 23 with superposed control punch margins 14, 14'. This superposition insures correct alignment during processing. Removal of the control punch margin 14' of the web 23 is advantageous where the labels have rounded corners——as illustrated. This develops an edge portion of the label which is free of any associated web material making finger insertion easy and facilitates removal of the label. However, where the corners are square, i.e., no rounded corners as at 36, the superposed web control punch margin 14' can be allowed to remain in place. With a straight line of demarcation between the control punch margin and the labels, it is easier to deform the web so as to "crack" the web and present a free edge on the label for fingernail insertion or grasping between forefinger and thumb. This is not so easily done, i.e., the "cracking," when the labels have rounded corners and the control punch margin 15' is characterized by a side having a cusp-like projection as at 37 in FIG. 2.

It has also been found advantageous to transversely sever the liner 16 along transverse lines in alignment with the line of perforation 12. This is illustrated in FIG. 8 as at 38 and the diecutting of the liner 16 can, if desired, be performed in the finishing station 35. This diecutting or slitting, may extend from the tip of the cusp as at 39 on one side to the tip of the cusp 40 on the other side of the label 25. This has been found to be effective in reducing the tendency of the composite product to "tent." Tenting phenomenon is usually a result of superposed webs being zig-zag folded where one web has to go around a larger radius than the other.

This slitting or substantial weakening so as to minimize tenting can be accompanied by pulsing of the adhesive applying nozzle 29 (via the valve 30) so as to provide a transverse interruption of adhesive as at 41. In any event, the liner 16 extends substantially along the length of each for length and may or may not be continuous web in the finished product, depending upon the character of the web material and its tendency to tent.

While in the foregoing specification a detailed description of the invention has been set down for the purpose of illustration, many variations in the details hereingiven may be made by those skilled in the art without departing from the spirit and scope of the invention.

We claim:

1. A label product comprising an elongated label stock web having a plurality of equally longitudinally spaced apart, transversely extending lines of perforation defining a string of connected form lengths, a release liner having a coating of release material on only one surface and being of a predetermined width, said label stock web having a width substantially greater than said predetermined width, uniform thickness pressure sensitive adhesive between said release liner one surface and said web, said release liner extending continuously over each of said form lengths, said release liner one surface having a longitudinally extending edge band free of release material whereby said web is permanently adhered to said release liner in said longitudinally extending edge band, and a perimetrically diecut label in said web in each form length spaced from said band and overlying said liner whereby said label is removed from said web and whereby said liner still remains attached to said web, said edge band being coextensive with said release liner.

2. The structure of claim 1 in which each form length includes a plurality of longitudinally related labels.

3. The structure of claim 1 in which each form length includes a single label extending generally over the form length.

4. The structure of claim 1 in which said label has a pair of longitudinally extending sides, one of said sides being adjacent said band, said liner having a line hole equipped control punch margin adjacent the other of said label longitudinally extending sides, said web terminating short of the line holes in said control punch margin.

5. The structure of claim 1 in which each label has rounded corners and a pair of transversely extending sides, a transversely extending side of one label being mutual with the transversely extending side of an adjacent label and said web presenting a cusp indentation adjacent the end of each transversely extending side.

* * * * *